US008632823B2

(12) United States Patent
Selkon

(10) Patent No.: US 8,632,823 B2
(45) Date of Patent: *Jan. 21, 2014

(54) TREATMENT OF INFECTED TISSUES WITH HYPOCHLOROUS ACID

(75) Inventor: Joe B. Selkon, Oxford (GB)

(73) Assignee: Puricore, Inc., Malvern, PA (US)

( * ) Notice: Subject to any disclaimer, the term of this patent is extended or adjusted under 35 U.S.C. 154(b) by 1124 days.

This patent is subject to a terminal disclaimer.

(21) Appl. No.: 11/962,464

(22) Filed: Dec. 21, 2007

(65) Prior Publication Data

US 2008/0160612 A1    Jul. 3, 2008

Related U.S. Application Data

(60) Continuation of application No. 11/844,826, filed on Aug. 24, 2007, which is a continuation of application No. 10/830,878, filed on Apr. 23, 2004, now Pat. No. 7,276,255, which is a division of application No. 10/084,518, filed on Feb. 25, 2002, now abandoned, which is a continuation of application No. PCT/GB00/03264, filed on Aug. 23, 2000.

(30) Foreign Application Priority Data

Aug. 23, 1999   (GB) .................................. 9919951.5

(51) Int. Cl.
  A61K 33/20   (2006.01)
  A61K 33/14   (2006.01)
  A61P 17/02   (2006.01)
  A61P 31/04   (2006.01)

(52) U.S. Cl.
  USPC ........... 424/661; 424/665; 514/925; 514/928; 514/944

(58) Field of Classification Search
  USPC .................. 424/661, 665; 514/925, 928, 944
  See application file for complete search history.

(56) References Cited

U.S. PATENT DOCUMENTS

| 5,427,667 | A  |   | 6/1995  | Bakhir et al. |
| 5,731,008 | A  |   | 3/1998  | Morrow |
| 6,333,054 | B1 |   | 12/2001 | Rogozinski |
| 6,426,066 | B1 |   | 7/2002  | Najafi et al. |
| 7,276,255 | B2 | * | 10/2007 | Selkon .......................... 424/665 |
| 2002/0160053 | A1 |   | 10/2002 | Yahagi et al. |
| 2003/0206882 | A1 | * | 11/2003 | Richter et al. ............. 424/70.24 |

FOREIGN PATENT DOCUMENTS

| DE | 3046324 A1 |   | 12/1982 |
| EP | 470841 |   | 2/1992 |
| EP | 0792584 A1 |   | 9/1997 |
| JP | 09-124431 |   | 5/1997 |
| JP | 09-183706 |   | 7/1997 |
| JP | 10-087462 |   | 4/1998 |
| JP | 10-236961 |   | 9/1998 |
| JP | 11-209292 |   | 8/1999 |
| WO | WO 99/34652 |   | 7/1999 |
| WO | WO 01/13926 | * | 3/2001 |

OTHER PUBLICATIONS

Selkon, J.B., et al., "Evaluation of the antimicrobial activity of a new super-oxidized water, Steriloxe®, for the disinfection of endoscopes," Journal of Hospital Infection, 41, pp. 59-70 (1999).
Shetty, N., et al., "Evaluation of the antimicrobial activity of a new disinfectant: Sterilox® 2500 against *Clostridium difficile* spores, *Helicobacter pylori*, vancomycin resistant *Enterococcus* species, *Candida albicans* and several *Mycobacterium* species," Journal of Hospital Infection, 41, pp. 101-105 (1999).
Tanaka, H., et al., "Antimicrobial activity of superoxidized water," Journal of Hospital Infection, 34, pp. 43-49 (1996).
Cherry, G. "GP guide to the care of patients with leg ulcers," Prescriber, pp. 71-76 and 81-83 (May 19, 1996).
Bunyan, J., "The treatment of burns by hypochlorite solution," Journal of Tropical Pediatrics, pp. 93-94 (1983).
"Dakin Cooper Stabilisé," Editions Du Vidal, p. 425, (1997) France.
Chemical Abstracts 127:39419 (1997).
Chemical Abstracts 124:66697 (1996).
Derwent Abstract 1999-497074; abstracting JP 11-209292 (Aug. 3, 1999).
JPAB Abstract JP404090760A (1992).
Stedman's Medical Dictionary, 26th ed., Williams & Wilkins, Baltimore (MD), 1995, pp. 465-466.
Tapper, R.C., et al., "Atomic force microscopy study of the biocidal effect of super-oxidised water, Sterilox", Biofilm Journal, vol. 3, Paper 4, (1998).
Eventov et al., "Detoxification and Disinfection With Sodium Hypochlorite," *Biomedical Engineering* vol. 32, No. 6, 1998.

\* cited by examiner

*Primary Examiner* — John Pak
(74) *Attorney, Agent, or Firm* — Cooley LLP

(57)  ABSTRACT

Super-oxidized water based on hypochlorous acid, such as is obtained by the electrochemical treatment of a saline solution, may be used in the treatment of leg ulcers or other open wounds. Preferably, the pH of the super-oxidized water is in a range of 4 to 7, and the water has a redox potential of >950 mV. Medicaments based on the super-oxidized water may be in liquid or gel form. The super-oxidized water is able to control the microbial population within the wound and at the same time permit cell proliferation.

8 Claims, 1 Drawing Sheet

Effect of super-oxidized water on dermal fibroblast proliferation

Effect of super-oxidized water on dermal fibroblast proliferation

TREATMENT OF INFECTED TISSUES WITH HYPOCHLOROUS ACID

CROSS-REFERENCE TO RELATED APPLICATIONS

This application is a continuation of application Ser. No. 11/844,826, filed Aug. 24, 2007, which is a continuation of application Ser. No. 10/830,878, filed Apr. 23, 2004, now U.S. Pat. No. 7,276,255, which is a divisional of application Ser. No. 10/084,518, filed Feb. 25, 2002, now abandoned, which is a continuation of PCT/GB00/03264, filed Aug. 23, 2000, which was published in the English language on Mar. 1, 2001 under International Publication No. WO 01/13926 A2, and the disclosure of which is incorporated herein by reference.

BACKGROUND OF THE INVENTION

This invention relates to mixtures of oxidants which are referred to in this specification as "super-oxidized water," a term which is known in the art.

Super-oxidized water may be used as a sterilizing, disinfecting and biocidal solution. One form of super-oxidized water is produced by the applicant under the trademark STERILOX®. This STERILOX super-oxidized water is generated at the point of use, for example in a hospital, by passing saline solution over coated titanium electrodes separated by a semi-permeable ceramic membrane at a current of about 6 to 9 Amps. An apparatus having coated titanium electrodes separated by a semi-permeable ceramic membrane is disclosed in the specifications of UK Patent Nos. 2253860 and 2274113. The basic structure of the apparatus is disclosed in GB2253860 and can be used to produce the STERILOX super-oxidized water.

STERILOX super-oxidized water contains a mixture of oxidizing species, predominantly hypochlorous acid (HOCl) and sodium hypochlorite. The STERILOX super-oxidized water has a pH of 5-7 and an oxidation reduction potential (redox) of around 1000 mV. The high redox potential allows for the quick and efficient destruction of microbes (bacteria, viruses, fungi and spores). Hypochlorous acid and hypochlorite are in equilibrium and the position of the equilibrium is determined solely by the pH.

Applicant has found that the resultant super-oxidized water is non-hazardous, non-irritating and non-sensitizing to the skin, non-irritating to the eyes, not harmful if swallowed and shows no evidence of mutagenic activity.

It is considered that hypochlorous acid exerts its biocidal effect by attacking the surface and plasma membrane proteins, impairing transport of solutes and the salt balance of bacterial cells (Pieterson et al, *Water SA*, 22(1): 43-48 (1996)). However, it is believed that HOCl does not enter freely into eukaryotic cells, which may explain the selectivity of hypochlorous solutions.

The STERILOX process produces an extremely effective sterilizing, cold, non-toxic solution, which is free from highly toxic chemicals and acts against a wide variety of bacteria, fungi, viruses and spores. The generation of STERILOX solutions requires only water, electricity and pure, vacuum-dried crystalline salt. Applicant considers that the STERILOX super-oxidized water will be suitable for a broad range of applications in both medical and non-medical environments, such as the preservation of poultry and fish and general agricultural and petrochemical uses, the breaking down of bacterial biofilm, water treatment and general disinfection in medical and veterinary applications. The STERILOX super-oxidized water has been found to be particularly useful for the disinfection of endoscopes which are sensitive to other cold disinfectants, such as peracetic acid, which are commonly used.

While glutaraldehyde may be used as a reliable disinfecting agent of flexible fiber-optic endoscopes and other heat-sensitive instruments, although being widely practiced in many hospitals, its use can cause asthma and dermatitis in healthcare staff as a result of exposure to glutaraldehyde fumes, hence a predilection to the use of peracetic acid and the relatively recent move towards the use of STERILOX super-oxidized water in such applications.

STERILOX super-oxidized water has been tested and is the subject of two scientific papers by Selkon et al, *Journal of Hospital Infection*, 41: 59-70 (1999) and Shetty et al, *Journal of Hospital Infection*, 41: 101-105 (1999). In these studies, freshly produced STERILOX super-oxidized water was found to be highly active against *Mycobacterium tuberculosis*, *Mycobacterium avium-intracellulare*, *Mycobacterium chelonae*, *Escherichia coli* (including type 0157), *Enterococcus faecalis*, *Pseudomonas aeruginosa*, *Bacillus subtilis* var *niger* spores, methicillin-resistant *Staphylococcus aureus*, *Candida albicans*, poliovirus type 2 and human immunodeficiency virus HIV-1.

There has been a recent upsurge in interest in the use of super-oxidized water as a disinfectant, because of its rapid and highly biocidal activity against a wide range of bacteria. Tanaka et al, *Journal of Hospital Infection*. 34: 43-49 (1996), report the electrolysis of a saline solution to produce a super-oxidized water with a highly acidic pH of 2.3-2.7, which limits its suitability for many applications, particularly the disinfection of endoscopes. The acidic pH of the super-oxidized water produced by the method described by Tanaka et al. also precludes its use in other medical indications.

Having carried out trials in a large number of applications, including those mentioned above, Applicant turned its attention to the use of STERILOX super-oxidized water as a disinfectant of mammalian tissue, in particular the treatment of open wounds such as leg ulcers.

An article by Chemy in *The Prescriber* (May 1996) entitled "GP guide to the care of patients with leg ulcers" states "leg ulcers are notoriously difficult to treat successfully and can seriously reduce the patient's quality of life." Indeed, according to Chemy, "epidemiological studies have shown that at any given time there are approximately 100,000 patients in the UK that have leg ulceration. In treating these patients it has been estimated that over £39 million per year alone is spent on materials used in their ulcer care."

There are two types of leg ulcers: arterial and venous. Arterial ulcers, which are much harder to treat, are caused by ischemia, while venous ulcers are caused by blood stasis in the veins.

There are many proposals for the management of ulcers, all of which have varying degrees of success. Successful ulcer management is very much dependent on the rigid adherence to a program of treatment in combination with effective disinfection of the wound, which reduces bacterial infection and promotes the regeneration of dermal fibroblasts and keratinocytes in the bed of the ulcer which are essential for healing of the wound and the growth of new tissue. If the bacterial growth is not controlled, the wound cannot heal.

The most useful treatment for venous ulcers is the use of compression bandages together with elevation of the leg(s). This mimics the pumping action of the calf muscles which return the blood back to the body and maximizes the removal of blood from the leg(s). In conjunction with this, other treatment strategies include the use of topical treatments such as GRANUFLEX® to aid granulation and skin repair, alginates to clean the wound of debris, dry inert dressings to protect the wound (but which do not promote healing), and bacteriostatic or bactericidal ointments to reduce the infection. While antibiotics have been used to reduce infection in the past, nowadays this is not a treatment of choice due to the increased risk of antibiotic resistance.

While potassium permanganate ($KMnO_4$) is an oxidant which has stood the test of time in the treatment of leg ulcers, it still nevertheless has the disadvantages of irritating and injuring newly grown skin and causing skin discoloration. Known hypochlorites, such as EUSOL (Edinburgh University Solution of Lime) and Daikin's solution, rely on a high concentration of hypochlorite ions for their disinfectant properties. In fact, these compounds are no longer recommended for use due to their irritant and painful effects and impairment of cell growth which outweigh their therapeutic value, resulting in these preparations falling out of use. Attempts have been made to reduce the alkaline effect of the high hypochlorite ion content of these Solutions, e.g. by the use of suitable buffers, but have been found to be ineffective in such circumstances.

All this has militated against the use of preparations including hypochlorites for the treatment of leg ulcers. However, the success in disinfection and sterilization of endoscopes and the known non-irritant effects of the STERILOX super-oxidized water, have led the Applicant to re-address the treatment of open wounds such as leg ulcers.

BRIEF SUMMARY OF THE INVENTION

As a first step, in vitro tests were carried out on single layers of cultured human dermal fibroblast cells and keratinocyte cells to ascertain whether or not super-oxidized water had any effect on the viability of the cells. The cells were incubated under sterile conditions in a super-oxidized water based on hypochlorous acid and including sodium hypochlorite and other oxidized chlorine species, having a pH range from 4 to 7 and a redox potential of around 1000 mV.

Surprisingly, Applicant found that there is an optimum pH at which cell growth is not inhibited despite there being other pH levels within the range at which the viability of the cells is impaired. Indeed, in view of the findings of Tanaka et al, Applicant expected that the lower pH range would be more effective.

The next step was crucial, because the applicant then had to ascertain whether or not the in vitro results could not only be replicated in vivo but also that there would be a sufficient biocidal effect to counteract any bacterial activity which would prejudice the viability of new cells. Accordingly, a clinical trial was carried out on a patient with chronic venous leg ulcers using freshly produced super-oxidized water based on hypochlorous acid having a pH of 5.4.

The patient did not experience any pain, and in fact commented that the treatment was comfortable and had a soothing effect. There was a positive effect on the bacterial flora as well as the clinical appearance of the wounds. No adverse effect was observed on the surrounding skin which, in a number of patients with long-standing ulcers, is often sensitive.

Applicant believes that the effects which have been observed can be explained by the low concentration of oxidized (free available) chlorine present in a super-oxidized water based on hypochlorous acid. This is in contrast to commonly known hypochlorite solutions which owe their biocidal activity to a high concentration of free chlorine (including hypochlorite) as indicated by their characteristic smell.

It could be said that Applicant has discovered a principle, which is that a balance between the biocidal effect and non-inhibition of cell growth enables the microbial population present in a wound to be controlled such as to allow cell growth to occur.

In order to carry this principle into effect and from one aspect of the invention, there is provided a super-oxidized water which is based on hypochlorous acid, acts as a biocide and allows cell growth. Expressed in another way, the present invention resides in a super-oxidized water in which the biocidal effect is due to hypochlorous acid and the non-inhibitory effect on cell growth is dependent on the level of the pH of the hypochlorous acid solution.

From a still further aspect of the invention, in a super-oxidized water based on hypochlorous acid and having a pH of 4 to 7, the solution has a pH selected in a range of about 4.3 to 6.2.

In a further aspect of the invention, there is provided, for use in the treatment of, or medicament for, skin ulcers or other open wounds, a super-oxidized water or other formulation, such as a gel, which is based on hypochlorous acid, acts as a biocide and allows cell growth. The super-oxidized water or other preparation based on hypochlorous acid may have a pH of 4 to 7, with the pH preferably being selected in a range of about 4.0 to 6.5, and more preferably in a range of about 4.0 to 6.2.

In any of the aspects of the invention defined above, the super-oxidized water has a biocide rate (D Value) of approximately 1 log unit reduction unit of *bacillus subtilis* spores in less than 1 minute with a 9:1 super-oxidized water: innoculum mix. A biocide rate of about 3.4 seconds may be achieved and is particularly preferred.

The super-oxidized water based on hypochlorous acid may be obtained by the electrolysis of a saline solution. Accordingly, from another aspect of the invention there is provided a method of obtaining a super-oxidized water based on hypochlorous acid, the method comprising passing the saline solution through an electrochemical cell having electrodes separated by a semi-permeable membrane and operating in such manner as to produce a super-oxidized water based on hypochlorous acid which acts as a biocide and allows cell growth.

In a preferred method of carrying out the invention, the super-oxidized water is obtained and the pH level of the solution is adjusted by a buffering action, which involves the use of an alkaline feed from the cell. By using an alkaline solution in this way, the addition of conventional buffers and the consequent expense is avoided.

While the pH of the super-oxidized water is preferably adjusted to be in a range of about 4.3 to 6.5, Applicant has found that, in the case of wounds, such as leg ulcers, it is advantageous if the pH is adjusted to about 5.4.

From a still further aspect, the invention resides in a method of producing a medicament containing super-oxidized water as defined above for use in the treatment of leg ulcers or other open wounds.

The invention also comprehends, in a super-oxidized water or other formulation having a pH of 4 to 7, the selection of a pH in a range of about 4.3 to 6.5, and preferably about 5.4, that is used for the treatment of leg ulcers or other open wounds.

By means of any of the aspects of the invention defined above, the disinfection of wounds such as leg ulcers is readily achieved without irritation and pain, the spread of infection is reduced, and cell growth and regeneration are facilitated, thereby enhancing healing. An added advantage is that there is no resistance or tolerance developed to disinfection which would occur with antibiotics.

Furthermore, the super-oxidized water of the invention lends itself readily to the treatment being carried out in many ways, although it has been found that a hydrobath in which the leg is immersed is soothing and generally pleasant for the patient. However, it should be appreciated that preparations other than solutions may be used, for example gels.

From yet another aspect, the invention also resides in a method of treating a human or animal body having a leg ulcer or other open wound using any of the super-oxidized water based on hypochlorous acid herein referred to above and any of the methods defined hereinabove.

Applicant believes that the present invention, in any or all of its aspects is a breakthrough and will revolutionize the treatment of open wounds, in particular leg ulcers, in a way which has been found to be impossible hitherto.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

In order that the invention may be more readily understood, reference will now be made, by way of example, to the accompanying examples, in which:

Example 1 describes an in vitro study, which investigated the effect of super-oxidized water based on hypochlorous acid on the proliferation of cultured human dermal fibroblast cells.

Example 2 describes an in vitro study, which investigated the cytotoxic effect of super-oxidized water based on hypochlorous acid on cultured human dermal fibroblast cells.

Example 3 describes an in vitro study, which investigated the effect of super-oxidized water based on hypochlorous acid on the proliferation of cultured human keratinocyte cells.

Example 4 describes a clinical trial of super-oxidized water on a patient with chronic leg ulcers.

EXAMPLE 1

Fibroblasts are flattened, irregular-shaped, connective tissue cells which are ubiquitous in fibrous connective tissue. They secrete components of the extracellular matrix, including collagen, and play an important role in tissue regeneration.

Three in vitro trials of super-oxidized water based on hypochlorous acid were carried out on single-layer cell cultures of human dermal fibroblast (HDF) cells to ascertain whether the super-oxidized water affected HDF cell proliferation. A range of dilutions of super-oxidized water at different pH levels was investigated.

Method

The super-oxidized water used in the trials was the product of the electrolysis of an aqueous saline solution passed over a mixture of proprietary catalysts on titanium electrodes to give a mixture of oxidizing species, particularly hypochlorous acid (HOCl) at a concentration of about 144 mg/l to 400 mg/l available free chlorine (Cl). The super-oxidized water was produced as required for each test; the apparatus (supplied by Sterilox Medical Limited, Abingdon, UK) was operated to give a final solution redox potential of >950 mV as recommended by the company. Appropriate dilutions of the super-oxidized water were made, and the pH of the final solution was adjusted using a phosphate buffer.

For the proliferation assay, HDF cells were seeded in normal (10%) fetal calf serum (FCS) and Dulbecco's Modified Eagle Medium (DMEM) at $1.5 \times 10^3$ cells/well. After 24 hours the medium was changed to low (0.4%) FCS/DMEM. After a further 48 hours incubation super-oxidized water at varying concentrations was added to the cells. The viability of the cells was observed, using a standard absorption assay, 3 and 6 days after the application of super-oxidized water.

Results i) Trial 1: HDF cells were incubated with super-oxidized water in a range of dilutions at a pH of 4.3. The dilutions used were: 1, 1/3, 1/7, 1/14, 1/28, 1/56, 1/112, 1/224, 1/448, 1/896, 1/1792 and 0.

Figure 1A:
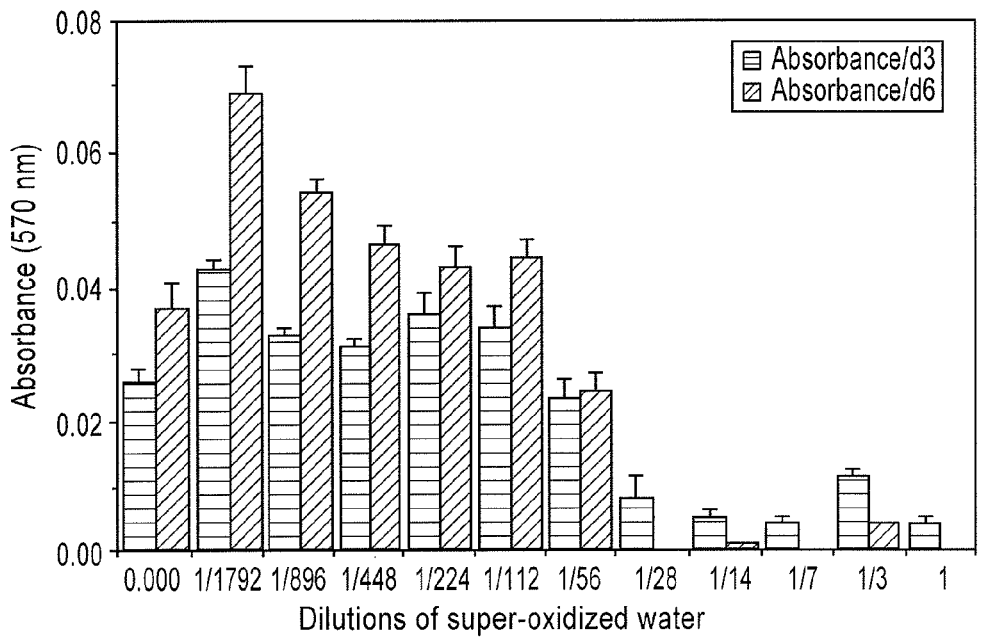
FIG. 1a is a bar graph illustrating the effect on dermal fibroblast proliferation, measured by absorption assay at 3 and 6 days, of various concentrations super-oxidized water.
Figure 1B:
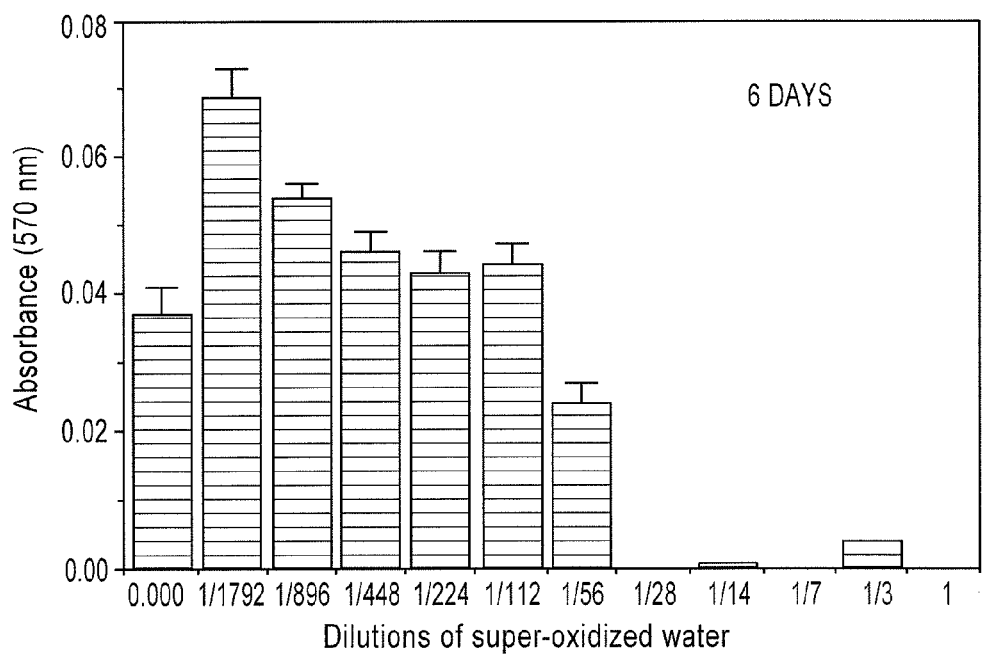
FIG. 1b is a bar graph similar to FIG. 1a, showing the results of the absorption assay at 6 days.

As shown in the accompanying graphs, on both day 3 (FIG. 1a) and day 6 (FIG. 1b) super-oxidized water dilutions of 1/28 or less significantly inhibited HDF proliferation or killed the cells. Slight inhibition of proliferation was seen at a dilution of 1/56. Dilutions of 1/112 to 1/448 showed no effect on proliferation, while the 1/896 dilution showed some cell proliferation and the dilution of 1/1792 showed significant proliferation of HDF cells.

These results show that high concentrations of super-oxidized water significantly inhibit HDF proliferation, probably because of the acidity, and therefore toxicity, of the super-oxidized water. The high level of proliferation seen with a concentration of super-oxidized water at 1/1792 may be attributed to other factors.

ii) Trial 2: Using the same conditions as Trial 1, HDF cells were incubated with super-oxidized water in a range of dilutions at a pH of 6.2. The dilutions used were: 1/20, 1/40, 1/60, 1/80, 1/100, 1/120, 1/1000, 1/1500, 1/2000, 1/3000, 1/4000 and 0.

No stimulation of proliferation was seen and indeed, inhibition of HDF growth was seen with cells incubated with a dilution of super-oxidized water of 1/20. However, the higher dilution of 1/40 showed no cell toxicity.

This trial was repeated with the HDF cells seeded in super-oxidized water at dilutions of 1, 1/4, 1/8, 1/12, 1/16, 1/20 (7 to 19 mg/l available free chlorine), 1/24 (6 to 16 mg/l available free chlorine), 1/28 and 1/32. After both day 3 and day 6, cell damage or inhibition of proliferation was seen at dilutions of 1/20 and below. However, dilution of more than 1/20 showed no damage or inhibition or proliferation.

In conclusion, while the more alkaline pH appears to be less toxic to HDF cells, proliferation of HDF cells is not seen at this pH.

iii) Trial 3: In this trial, two plates of cells were grown always in normal growth medium (10% FCS/DMEM). One plate of cells was treated as described in Trial 1 but after three days of incubation with the super-oxidized water, the growth medium was changed from 0.4% FCS/DMEM to 10% FCS/DMEM in order to observe the recovery of the cells.

HDF cells were incubated at 31° C. with super-oxidized water in a range of dilutions at a pH of 5.4. The dilutions used were: 1/10 (13 to 36 mg/l available free chlorine), 1/20 (7 to 19 mg/l available free chlorine), 1/40 (4 to 10 mg/l available free chlorine), 1/60, 1/80, 1/100, 1/150, 1/1000, 1/1500, 1/2000, 1/4000 and 0.

On day 3 and day 6 cell proliferation was seen in cells incubated with super-oxidized water at a dilution of 1/20 or higher in either 0.4% or 10% FCS/DMEM. Some levels of proliferation had reached statistical significance. A dilution of 1/10 super-oxidized water inhibited cell growth in HDF cells grown in 0.4% FCS/DMEM but not in 10% FCS/DMEM.

After 3 days incubation in 0.4% FCS/DMEM with or without super-oxidized water, the medium was changed to 10% FCS/DMEM. The cells that had been incubated with super-oxidized water showed the same ability to recover from depression of cell growth seen while growing in 0.4% FCS/DMEM as control cells.

This trial was repeated with the HDF cells seeded in super-oxidized water at dilutions of 1/7 (18 to 50 mg/l available free chlorine), 1/10 (13 to 36 mg/l available free chlorine), 1/15 (9 to 25 mg/l available free chlorine), 1/20 (7 to 19 mg/l available free chlorine), 1/40 (4 to 10 mg/l available free chlorine), 1/60, 1/100, 1/500, 1/1000, 1/2000, 1/4000 and 0.

Again, on both day 3 and day 6, cell proliferation was seen with HDF cells grown in 0.4% FCS/DMEM with the difference seen being statistically significant at most dilutions. No inhibition of cell growth was seen, even at the dilution of 1/7 super-oxidized water. Stimulation of cell growth was also seen in cells grown in 10% FCS/DMEM in the presence of super-oxidized water. However, the levels of proliferation did not reach statistical significance. Where cell growth had been impaired by incubation with super-oxidized water, recovery was seen, confirming the observations from the first set of experiments.

In summary, HDF cells incubated with super-oxidized water at pH 5.4 showed no inhibition of cell growth, even in the presence of a 1/7 dilution of super-oxidized water.

CONCLUSION

The presence of super-oxidized water at a pH of 5.4 does not inhibit HDF cell growth in vitro.

EXAMPLE 2

Three in vitro trials were carried out to investigate the cytotoxic effect of super-oxidized water based on hypochlorous acid on HDF cells.

Method

The super-oxidized water based on hypochlorous acid was identical to that described in Example 1.

HDF cells were seeded in 10% FCS/DMEM at $5 \times 10^3$ cells/well. After incubation at 31° C. for 72 hours, dilutions of super-oxidized water were prepared in HBSS and added to the cells. The viability of the cells was ascertained by a standard absorption assay at time intervals of 15 minutes up to one hour from the addition of the super-oxidized water.

Results i) Trial 1: HDF cells were incubated with super-oxidized water in a range of dilutions at a pH of 4.3. The dilutions used were: 1, 1/3, 1/7, 1/14, 1/28, 1/56, 1/112, 1/224, 1/448, 1/896, 1/1792 and 0.

No effect on cell viability was seen in the presence of super-oxidized water at dilutions of 1/28 or more at any of the time points. A dilution of 1/14 induced mild damage to the cells while dilutions of 1/7 and less killed the cells.

ii) Trial 2: Using the same conditions as trial 1, HDF cells were incubated with super-oxidized water in a range of dilutions at a pH of 6.2. The dilutions used were: 1, 1/4, 1/8, 1/12, 1/16, 1/20, 1/24, 1/28, 1/32, 1/36, 1/40 and 0.

No significant effect was seen on the viability of HDF cells in the presence of super-oxidized water at dilutions of 1/20 or more at any time point. However, dilution of 1/16 or less induced cell damage.

iii) Trial 3: Using the same conditions as Trials 1 and 2, HDF cells were incubated with super-oxidized water in a range of dilutions at a pH of 4.0. The dilutions used were: 1, 1/4, 1/8, 1/12, 1/16, 1/20, 1/24, 1/28, 1/50, 1/100, 1/200 and 0.

Dilutions of super-oxidized water at 1/24 and 1/20 induced slight damage to the cells while dilution of 1/16 or less induced cell death.

CONCLUSION

The results of these trials support the results shown in Example 1 in that, while super-oxidized water at pH 4.0 to 4.3 and pH 6.2 induce damage to cultured HDF cells, greater cytotoxic effects are seen at the lower pH.

EXAMPLE 3

In view of the results described in Examples 1 and 2, two in vitro trials were carried out to investigate the effect super-oxidized water on human keratinocyte (HK) cell proliferation. The super-oxidized water used in these trials was identical to that described in Example 1. Keratinocytes are epidermal skin cells that synthesize keratin and, together with dermal fibroblasts, are essential for skin healing.

Trial 1

HK cells (subcultured, P2, FS, 7 years) were seeded at $8 \times 10^3$ cells/well and incubated at 31° C. in CLONETICS® (Biowhittaker, US) serum-free medium with complete supplements, hereinafter referred to as keratinocyte growth medium (KGM), in four 24-well plates. After 24 hours incubation the medium in plates 1 and 2 was changed to CLONETICS® (Biowhittaker, US) serum-free medium without complete supplements, hereinafter referred to as keratinocyte basal medium (KBM).

After a further 48 hours incubation super-oxidized water diluted in KBM at pH 5.4 was added to plates 1 and 2, and super-oxidized water diluted in KGM was added to plates 3 and 4. The dilutions of super-oxidized water were: 1/10, 1/20, 1/50, 1/100, 1/150, and 0. The pH of the final super-oxidized water solution was adjusted using a phosphate buffer.

After incubation for a further 3 days a standard absorption assay was carried out on plate 3 to observe the viability and growth of the cells. The absorption assay was carried out on plate 4 after a still further two days. Since the cells incubated in KBM did not grow well, plates 1 and 2 were discarded.

The absorption assay showed that, on both day 3 and day 5, cell proliferation had occurred in the presence of all dilutions of super-oxidized water. At day 5, the level of cell proliferation had reached a significant level compared to cell growth in the absence of super-oxidized water.

Trial 2

In view of the fact that the HK cells did not grow in KBM and showed significant proliferation in the presence of super-oxidized water in KGM, it was decided to use KBM with lower concentrations of supplements as a holding medium, with or without super-oxidized water.

HK cells (thawed, P2, FS, 7 years) were seeded to six 96-well plates at $3 \times 10^3$ cells/well in KGM. After incubation for 24 hours, the medium in plates 1 and 2 was changed to KBM with 20% supplements, and the medium in plates 3 and 4 was changed to KBM with 50% supplements.

After incubation for a further 24 hours, super-oxidized water diluted in KBM with 20% supplements was added to plates 1 and 2, super-oxidized water diluted in KBM with 50% supplements was added to plates 3 and 4, and plates 5 and 6 received super-oxidized water diluted in complete KGM. The dilutions of super-oxidized water were: $1/7$, $1/10$, $1/15$, $1/20$, $1/40$, $1/60$, $1/100$, $1/500$, $1/1000$, $1/2000$, $1/4000$ and 0.

The cells were incubated for a further 3 days in the presence of super-oxidized water, after which time, a standard absorption assay was carried out on plates 1, 3 and 5 to ascertain the viability of the cells, and the medium in plates 2, 4 and 6 was changed to KGM. Plates 2, 4 and 6 were assayed after a further 48 hours of incubation.

Stimulation of cell proliferation on both day 3 and day 5 was seen in all percentages of KGM supplements. However, the level of stimulation was not significantly different when compared to control cell growth. No cytotoxicity was seen even at the low dilution of $1/7$ super-oxidized water.

CONCLUSION

Dermal keratinocytes cultured in the presence of KGM and super-oxidized water showed enhanced cell proliferation, and no cytotoxicity was seen in the presence of super-oxidized water.

EXAMPLE 4

A preliminary clinical evaluation of super-oxidized water based on hypochlorous acid was carried out on one patient with chronic venous ulcers on both left and right legs. The aim of the trial was to determine whether the bacterial status of the ulcers is altered and the bed of the ulcer improved by treatment with super-oxidized water.
Method The patient's legs were immersed in 40 liters of super-oxidized water in a hydrobath for fifteen minutes before being allowed to dry. An intermediate assessment without treatment was carried out after one week.

A second treatment with super-oxidized water was repeated after two weeks in which the patient was subjected to three fifteen-minute washes at approximately three-hour intervals. Post-treatment clinical evaluation was carried out one and several days after the second treatment.

Semi-quantitative microbiological analysis of the leg ulcers was carried out on swabs taken before and fifteen minutes after treatment with super-oxidized water.
Results After the first treatment, the patient reported that the treatment was comfortable and free from pain. The appearances of the ulcers on both legs were markedly improved when assessed five hours after treatment.

As shown in Table 1, quantitative microbiology showed a reduction in the number of colony-forming units in the order of $10^2$ in the right leg ulceration and a reduction in the order of $10^4$ on the left leg.

TABLE 1 semi-quantitative microbiological analysis of leg ulcers before and after treatment with super-oxidized water based on hypochlorous acid. Figures quoted indicate the number of colony-forming units (cfu) per ml.

|  | Right Leg | Left Leg |
|---|---|---|
| Pre-treatment | $1 \times 10^7$ | $1 \times 10^7$ |
| Post-treatment | $1 \times 10^5$ | $1 \times 10^3$ |

The patient was seen one week after the first treatment and was treated with conventional therapy, including potassium permanganate. The effect of these on the appearance of the leg ulcers following treatment did not appear to be as striking as that seen with super-oxidized water.

A second treatment with super-oxidized water was repeated a further week later, and similar beneficial results were obtained. In between the treatment periods the ulcers had become sloughy on both legs. Immediately after the first wash, the ulcer bed was whitish due to effervescence. A cleansing effect was seen after the later two washes, and a marked improvement was seen with the state of the ulcer 18 hours after the first wash.

The patient reported no discomfort to the treatment, the solution in the bath was soothing, and the skin felt a bit tight afterwards. The patient commented that the tightness started to be felt once cold air was accessible to the skin.

Referring to Table 2, quantitative microbiology showed a reduction in the number of colony-forming units in the order of $10^2$ in the right leg ulceration and a reduction in the order of $10^4$ on the left leg.

TABLE 2 semi-quantitative microbiological analysis of leg ulcers before and after treatment with super-oxidized water based on hypochlorous acid. Figures quoted indicate the number of colony-forming units (cfu) per ml.

|  | Right leg (cfu/ml) | organisms found | Left leg (cfu/ml) | organisms found |
|---|---|---|---|---|
| pre-treatment 1 | $1.9 \times 10^8$ | Coliforms *Proteus* spp skin flora | $4.5 \times 10^6$ | Coliforms *Proteus* spp skin flora |
| post-treatment 1 | $1.2 \times 10^5$ | Coliforms skin flora *Proteus* spp | $4.5 \times 10^4$ | skin flora β-haemolytic streptococci Coliforms *Proteus* spp |
| pre-treatment 2 | $3.0 \times 10^3$ | Coliforms *Proteus* spp skin flora | $1.5 \times 10^4$ | Coliforms skin flora |
| post-treatment 2 | $1 \times 10^3$ | Coliforms *Proteus* spp skin flora | <10 | no growth |
| pre-treatment 3 | <10 | no growth | $6.3 \times 10^3$ | Coliforms β-haemolytic streptococci skin flora |
| post-treatment 3 | $3.0 \times 10^2$ | Coliforms skin flora *Proteus* spp | $3.0 \times 10^3$ | β-haemolytic streptococci |
| post 24 hours | $2.7 \times 10^2$ | Coliforms *Proteus* spp skin flora | $1.5 \times 10^6$ | β-haemolytic streptococci Coliforms *Proteus* spp |

CONCLUSION

The main objectives of the clinical study were to examine patient comfort and safety, as well as the efficiency of a treatment of super-oxidized water based on hypochlorous acid.

The use of antiseptics for cleansing wounds is controversial, particularly with reference to the degree of pain associated with this kind of treatment. This patient did not experience pain and, in fact, commented on a soothing effect. There was a positive effect on the bacterial flora as well as the clinical appearance of the wounds. There was no adverse effect on the surrounding skin which, in a number of patients with long-standing ulcers, is often sensitive.

While the invention has been described with reference to the examples in relation to the treatment of leg ulcers, it should be appreciated that the invention has considerably wider applicability. For example, the invention has applicability to burns, to organ transplants in relation to which current practice is to disinfect organs with antibiotics for two weeks before they are used in a patient, to disinfection of valve-replacements, and to surface wounds, open wounds and plural cavity infections which are exhibiting drug-resistance.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for disinfecting a mammalian tissue comprising dermal fibroblasts, the method comprising:
    administering a hypochlorous acid formulation to said tissue in an amount effective to act as a microbiocide without inhibiting growth of said dermal fibroblasts;
    wherein the formulation is obtained by (i) electrolysis of an aqueous saline solution to provide an output hypochlorous acid solution having an available free chlorine concentration of 144 mg/L to 400 mg/L and a redox potential of >950 mV, and (ii) diluting said output solution and adjusting its pH such that the pH is within 5 to 7.

2. The method of claim 1, wherein the mammalian tissue comprises a surface or open wound.

3. The method of claim 2, wherein the mammalian tissue comprises a leg ulcer.

4. The method of claim 1, wherein the mammalian tissue comprises a burn.

5. The method of claim 3 or 4, wherein the formulation has a pH of about 5.4 or about 6.2.

6. The method of claim 1, wherein the formulation is formulated as a gel.

7. The method of claim 1, wherein the output hypochlorous acid solution is produced in an electrochemical cell having electrodes separated by a semi-permeable membrane.

8. The method of claim 1, wherein the mammalian tissue further comprises keratinocytes.

* * * * *